United States Patent [19]

Jahn et al.

[11] Patent Number: 4,654,073
[45] Date of Patent: * Mar. 31, 1987

[54] CYCLOHEXANE-1,3-DIONE DERIVATIVES AND THEIR USE FOR CONTROLLING UNDESIRABLE PLANT GROWTH

[75] Inventors: Dieter Jahn, Edingen-Neckarhausen; Rainer Becker, Bad Duerkheim; Michael Keil, Freinsheim; Winfried Richarz, Stockstadt; Hardo Siegel, Speyer; Wolfgang Spiegler, Worms; Bruno Wuerzer, Otterstadt, all of Fed. Rep. of Germany

[73] Assignee: Basf Aktiengesellschaft, Fed. Rep. of Germany

[*] Notice: The portion of the term of this patent subsequent to Dec. 27, 2000 has been disclaimed.

[21] Appl. No.: 666,908

[22] Filed: Oct. 31, 1984

[30] Foreign Application Priority Data

Nov. 8, 1983 [DE] Fed. Rep. of Germany ....... 3340265

[51] Int. Cl.$^4$ .................... A01N 43/00; A01N 43/02; C07D 321/00; C07D 309/00
[52] U.S. Cl. .......................................... 71/88; 549/13; 549/14; 549/22; 549/39; 549/347; 549/373; 549/378; 549/426; 71/90
[58] Field of Search ............... 549/347, 426, 14, 22, 549/39, 373, 378; 71/88

[56] References Cited

U.S. PATENT DOCUMENTS 3,950,420  4/1976  Sawaki et al. .......................... 71/88
3,989,737  11/1976  Sawaki et al. .......................... 71/88
4,422,864  12/1983  Becker et al. .......................... 549/347
4,596,877  6/1986  Becker et al. .......................... 71/90

FOREIGN PATENT DOCUMENTS 1461170  1/1977  United Kingdom .................... 83/6

Primary Examiner—Ethel G. Love
Attorney, Agent, or Firm—Keil & Weinkauf

[57] ABSTRACT

Cyclohexane-1,3-dione derivatives of the formula

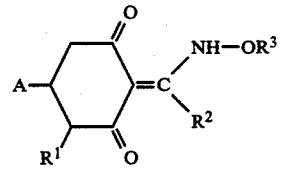

where A is tetrahydropyran-4-yl, 3-methyltetrahydropyran-4-yl, 1,4-dioxanyl, 5,5-dimethyl-1,3-dioxan-2-yl, 2,5-dimethyl-1,4-dioxan-3-yl, 2,6-dimethyl-1,4-dioxan-3-yl, 2-methyl-1,3-dithiolan-2-yl, 2,6-dimethyltetrahydrothiopyran-3-yl, 2-methyl-1,3-dithian-2-yl or unsubstituted or substituted 1,3-dioxepan-5-yl, $R^1$ is hydrogen or methoxycarbonyl, $R^2$ is alkyl and $R^3$ is alkyl, alkenyl, haloalkenyl or propargyl, are used for controlling undesirable plant growth of grass species, especially in broadleaved crops and monocotyledon crops which do not belong to the grass family.

10 Claims, No Drawings

CYCLOHEXANE-1,3-DIONE DERIVATIVES AND THEIR USE FOR CONTROLLING UNDESIRABLE PLANT GROWTH

The present invention relates to cyclohexane-1,3-dione derivatives, and herbicides which contain these compounds as active ingredients.

It is known that cyclohexane-1,3-dione derivatives can be used for controlling undesirable grasses in broad-leaved crops. Active ingredients possessing furyl or thienyl substituents have a relatively weak action (German Laid-Open Application DOS No. 2,439,104). Moreover, European Laid-Open Application No. 0,071,707 discloses heterocyclically substituted cyclohexane-1,3-dione derivatives which possess a good herbicidal action against plants from the grass family.

We have found that novel cyclohexane-1,3-dione derivatives which carry certain heterocyclic substituents in the 5-position have substantially greater herbicidal action than the prior art active ingredients against a number of grass species (wild and cultivated species). These compounds are very well tolerated by both broadleaved crop plants and monocotyledon crops which do not belong to the grass family. Moreover, in spite of having a good action against grasses, some of these compounds are also tolerated by the crop plant wheat when they are used in certain doses.

The novel cyclohexane-1,3-dione derivatives are of the formula

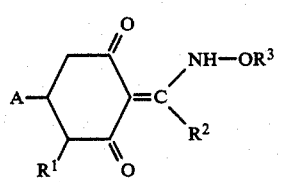
(I)

where A is tetrahydropyran-4-yl, 3-methyltetrahydropyran-4-yl, 1,4-dioxanyl, 5,5-dimethyl-1,3-dioxan-2-yl, 2,5-dimethyl-1,4-dioxan-3-yl, 2,6-dimethyl-1,4-dioxan-3-yl, 2-methyl-1,3-dithiolan-2-yl, 2,6-dimethyltetrahydrothiopyran-3-yl or 2-methyl-1,3-dithian-2-yl, or is 1,3-dioxepan-5-yl which is unsubstituted or substituted by alkyl of 1 to 8 carbon atoms, by alkylene of 4 or 5 carbon atoms or by unsubstituted or methyl-substituted cycloalkyl or bicycloalkyl of 6 to 12 carbon atoms, $R^1$ is hydrogen or methoxycarbonyl, $R^2$ is alkyl of 1 to 4 carbdn atoms and $R^3$ is alkyl of 1 to 4 carbon atoms, alkenyl of 3 or 4 carbon atoms, haloalkenyl of 3 or 4 carbon atoms and 1 to 3 halogen substituents, or propargyl.

The compounds of the formula I can occur in a number of forms, all of which are within the scope of the invention claimed:

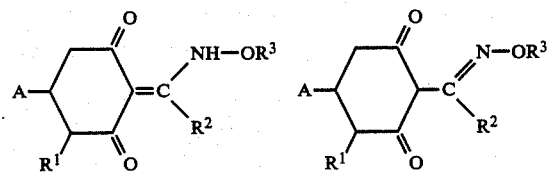

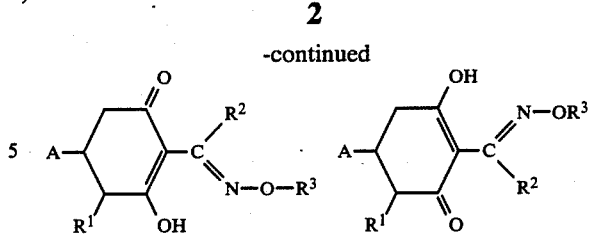

The 1,3-dioxepan-5-yl radicals A in formula I can be substituted by straight-chain or branched alkyl of 1 to 8 carbon atoms, e.g. methyl, ethyl, isopropyl, tert.-butyl, 1,2-dimethylbut-4-yl or 1-ethyl-n-pentyl, or by cycloalkyl or bicycloalkyl of 6 to 12 carbon atoms, e.g. cyclohexyl, cycloheptyl, cyclooctyl, cyclododecyl or bicycloheptyl such as bicyclo[3.1.1]heptyl. The cycloalkyl and bicycloalkyl radicals may furthermore carry one or more methyl substituents. Moreover, the 1,3-dioxepan-5-yl radicals can be substituted by alkylene of 4 or 5 carbon atoms, i.e. tetramethylene or pentamethylene, so that, for example, spiro compounds are formed.

In formula I, $R^2$ is straight-chain or branched alkyl of 1 to 4 carbon atoms, i.e. methyl, ethyl, n-propyl, isopropyl, n-butyl, sec.-butyl, isobutyl or tert.-butyl, and $R^3$ is propargyl, alkyl of 1 to 4 carbon atoms, alkenyl of 3 or 4 carbon atoms or haloalkenyl of 3 or 4 carbon atoms which can contain not more than three halogen substituents, e.g. chlorine, bromine or fluorine, examples of radicals being methyl, ethyl, n-propyl, isopropyl, n-butyl, sec.-butyl, isobutyl, tert.-butyl, allyl, 1-chloroprop-1-en-3-yl, 2-chloroprop-1-en-3-yl, 1,3-dichloroprop-1-en-3-yl and 1,2,3-trichloroprop-1-en-3-yl.

Preferred cyclohexane-1,3-dione derivatives of the formula I are those in which $R^1$ is hydrogen and those in which $R^2$ is alkyl of 2 or 3 carbon atoms. Preferred radicals A are tetrahydropyran-4-yl, 2,6-dimethyltetrahydrothiopyran-3-yl, and 1,3-dioxepan-5-yl which is unsubstituted or substituted by alkyl of 1 to 8, in particular 1 to 4, carbon atoms, by alkylene of 4 or 5 carbon atoms or by unsubstituted or methyl-substituted cycloalkyl or bicycloalkyl of 7 to 12 carbon atoms, in particular 1,3-dioxepan-5-yl which is unsubstituted or substituted by straight-chain or branched alkyl of 1 to 4 carbon atoms.

Examples of suitable salts of the compounds of the formula I are the alkali metal salts, in particular the potassium and sodium salts, the alkaline earth metal salts, in particular calcium, magnesium and barium salts, manganese, copper, zinc and iron salts, ammonium and phosphonium salts, e.g. alkylammonium, dialkylammonium, trialkylammonium, tetraalkylammonium, benzyltrialkylammonium and triphenylphosphonium salts, and trialkylsulfonium and trialkylsulfoxonium salts.

The compounds of the formula I can be obtained by reacting a compound of the formula

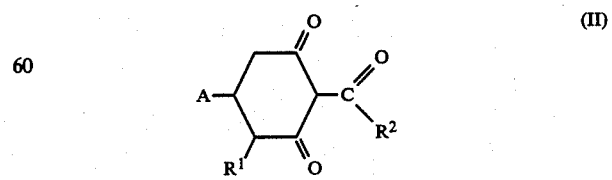
(II)

where A, $R^1$ and $R^2$ have the above meanings, with a hydroxylamine derivative $R^3O-NH_3Y$, in which $R^3$ has the above meanings and Y is an anion.

The reaction is advantageously carried out in the heterogeneous phase in an inert diluent at from 0° to 80° C. or from 0° C. to the boiling point of the reaction mixture, in the presence of a base. Examples of suitable bases are carbonates, bicarbonates, acetates, alcoholates, hydroxides and oxides of alkali and alkaline earth metals, in particular of sodium, potassium, magnesium and calcium. It is also possible to use an organic base, e.g. pyridine or a tertiary amine.

Examples of suitable solvents are dimethyl sulfoxide, alcohols, such as methanol, ethanol or isopropanol, benzene, hydrocarbons and chlorohydrocarbons, such as chloroform, dichloroethane, hexane or cyclohexane, esters, such as ethyl acetate, and ethers, such as dioxane or tetrahydrofuran.

The reaction is complete after a few hours, and the product can then be isolated by evaporating down the mixture, adding water, extracting with a nonpolar solvent, such as methylene chloride, and distilling off the solvent under reduced pressure.

The compounds of the formula I can furthermore be obtained by reacting a compound of the formula II with a hydroxylamine of the formula $R^3O-NH_2$, in which $R^3$ has the above meanings, in an inert diluent at from 0° C. to the boiling point of the reaction mixture, in particular from 15° to 70° C. If necessary, the hydroxylamine can be used in the form of an aqueous solution.

Examples of suitable solvents for this reaction are alcohols, such as methanol, ethanol, isopropanol or cyclohexanol, hydrocarbons and chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

The alkali metal salts of the compounds of the formula I can be obtained by treating these compounds with sodium hydroxide or potassium hydroxide in aqueous solution or in an organic solvent, such as methanol, ethanol or acetone. It is also possible to use a sodium alcoholate or potassium alcoholate as the base.

The other metal salts, e.g. the manganese, copper, zinc, iron, calcium, magnesium and barium salts, can be prepared from the sodium salts by reaction with the corresponding metal chlorides in aqueous solution. Ammonium, sulfonium, sulfoxonium and phosphonium salts can be prepared by reacting a compound of the formula I with an ammonium, phosphonium, sulfonium or sulfoxonium hydroxide, if necessary in aqueous solution.

The compounds of the formula II can be prepared, using a conventional method (Tetrahedron Lett. 29 (1975), 2491), from a cyclohexane-1,3-dione of the formula III, which may also occur in the tautomeric forms of the formulae IIIa and IIIb:

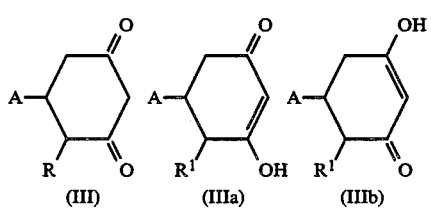

It is also possible to prepare compounds of the formula II via the intermediate stage of the enol esters, which are obtained, possibly as isomer mixtures, in the conversion of compounds of the formula III, and undergo rearrangement in the presence of an imidazole or pyridine derivative (Japanese Preliminary Published Application No. 79/063,052).

Compounds of the formula III are obtained by processes known from the literature, as can be seen from the equations below:

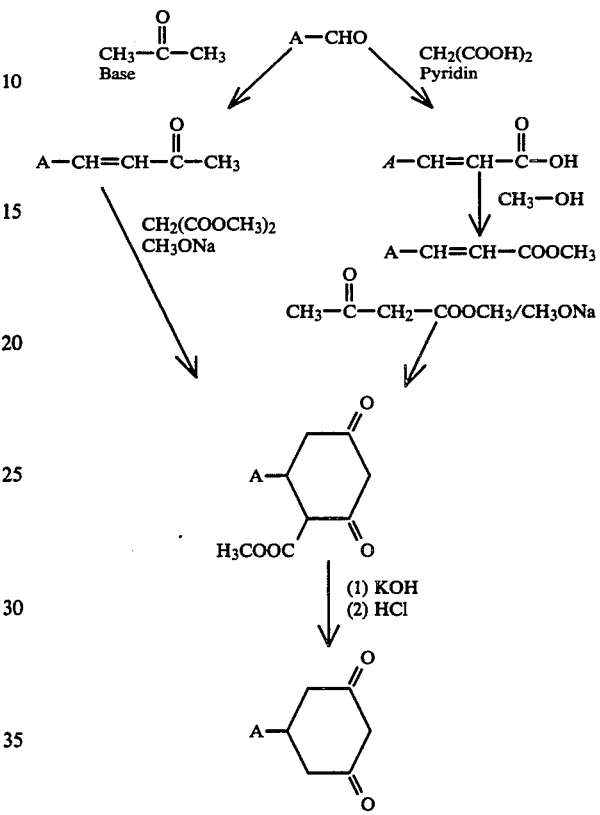

Aldehydes of the general formula A—CHO are obtained by processes known from the literature, for example by oxidation of the corresponding alcohols, reduction of carboxylic acid derivatives or hydroformylation of olefins.

The Examples which follow illustrate the preparation of the cyclohexane-1,3-dione derivatives of the formula I. Parts by weight bear the same relation to parts by volume as that of the kilogram to the liter.

The $^1H$-NMR spectra were recorded using deuterochloroform as a solvent and tetramethylsilane as an internal standard. The $^1H$ chemical shifts are stated as δ [ppm] in each case. The following abbreviations have been used to indicate the signal structure: s=singlet, d=doublet, t=triplet, q=quartet, m=multiplet, strongest signal.

EXAMPLE 1

6.5 parts by weight of 2-butyryl-5-(2-isopropyl-1,3-dioxepan-5-yl)-cyclohexane-1,3-dione, 2.1 parts by weight of ethoxyammonium chloride and 1.8 parts by weight of sodium bicarbonate in 80 parts by volume of methanol are stirred for 16 hours at room temperature. The solvent is distilled off under reduced pressure, the residue is stirred with 50 parts by volume of water and 50 parts by volume of dichloromethane, the organic phase is separated off, the aqueous phase is extracted once with 50 parts by volume of dichloromethane, the combined organic phases are dried over sodium sulfate, and the solvent is distilled off under reduced pressure. 6.2 parts by weight of 2-(1-ethoxyamino-n-butylidene)-5-(2-isopropyl1,3-dioxepan-5-yl)-cyclohexane-1,3-dione are obtained as an oil (active ingredient No. 1).

$n^{26}$: 1.514.

$^1H^D$-NMR spectrum: $\delta$=0.90 (d), 1.18 (t), 2.45 (q), 4.15 (q).

EXAMPLE 2

14.0 parts by weight of 2-butyryl-5-(tetrahydropyran-4-yl)-cyclohexane-1,3-dione and 4.2 parts by weight of allyloxyamine in 100 parts by volume of methanol are stirred for 16 hours at room temperature. The solvent is distilled off under reduced pressure, the residue is dissolved in dichloromethane, the solution is then washed with 5% strength hydrochloric acid and water and dried over sodium sulfate, and the solvent is stripped off under reduced pressure to give 12.9 parts by weight of 2-(1-allyloxyamino-n-butylidene)-5-(tetrahydropyran-4-yl)cyclohexane-1,3-dione in the form of a solid (active ingredient No. 2).

Mp. 55°–56° C.:

$^1$H-NMR spectrum $\delta$=0.95 (t), 2.85 (t), 3.40 (t), 4.55 (d).

The compounds below can be obtained in the same manner:

| Compound no. | A | $R^1$ | $R^2$ | $R^3$ | $^1$H-nmr data ($\delta$ values)/$n_D$/m.p. |
|---|---|---|---|---|---|
| 3 | 4-tetrahydropyranyl | H | n-propyl | ethyl | n.p. 48–50° C. |
| 4 | 4-tetrahydropyranyl | H | ethyl | ethyl | 1.70 (d), 2.95 (q), 3.4 (t) |
| 5 | 4-tetrahydropyranyl | H | ethyl | allyl | 1.15 (t), 2.90 (q), 4.55 (d) |
| 6 | 5,5-dimethyl-1,3-dioxan-2-yl | H | n-propyl | allyl | 0.65 (s), 1.10 (s), 2.85 (m) |
| 7 | 5,5-dimethyl-1,3-dioxan-2-yl | H | n-propyl | ethyl | m.p. 51° C. |
| 8 | 2,6-dimethyltetrahydrothio-pyran-3-yl | H | n-propyl | ethyl | |
| 9 | 2,6-dimethyltetrahydrothio-pyran-3-yl | H | n-propyl | allyl | |
| 10 | 2,5-dimethyl-1,4-dioxan-3-yl/2,6-dimethyl-1,4-dioxan-3-yl (isomer mixture) | H | n-propyl | allyl | 0.98 (t), 1.07 (d), 2.90 (t) 4.55 (d) |
| 11 | 2,5-dimethyl-1,4-dioxan-3-yl/1,6-dimethyl-1,4-dioxan-3-yl (isomer mixture) | H | n-propyl | ethyl | 0.95 (t), 1.07 (d), 1.30 (t), 4.12 (g) |
| 12 | 1,4-dioxanyl | H | n-propyl | ethyl | $n_D^{22}$ = 1.5226 |
| 13 | 1,4-dioxanyl | H | n-propyl | allyl | $n_D^{22}$ = 1.5229 |
| 14 | 1,4-dioxanyl | H | n-propyl | 3-chloro-allyl | $n_D^{22}$ = 1.5391 |
| 15 | 1,4-dioxanyl | H | ethyl | ethyl | $n_D^{22}$ = 1.5259 |
| 16 | 1,4-dioxanyl | H | ethyl | allyl | |
| 17 | 2-isopropyl-1,3-dioxepan-5-yl | H | ethyl | ethyl | 0.90 (d), 1.14 (t), 1.32 (t) 2.45 (q), 4.30 (m) |
| 18 | 1,3-dioxepan-5-yl | H | n-propyl | ethyl | 1.30 (t), 1.70 (m), 4.7 (s) |
| 19 | 1,3-dioxepan-5-yl | H | n-propyl | allyl | 0.9 (t), 1.70 (m), 3.8 (m) |
| 20 | 1,3-dioxepan-5-yl | H | ethyl | allyl | 1.15 (t), 1.70 (m), 2.9 (q) |
| 21 | 1,3-dioxepan-5-yl | H | ethyl | ethyl | 1.7 (m), 3.8 (m), 4.65 (s) |
| 22 | 2-methyl-1,3-dioxepan-5-yl | H | ethyl | ethyl | 1.1 (t), 1.7 (m), 2.9 (q) |
| 23 | 2-methyl-1,3-dioxepan-5-yl | H | ethyl | allyl | |
| 24 | 2-methyl-1,3-dioxepan-5-yl | H | n-propyl | ethyl | 0.9 (t), 4.1 (q), 4.9 (m) |
| 25 | 2-methyl-1,3-dioxepan-5-yl | H | n-propyl | allyl | 0.9 (t), 2.65 (m), 4.5 (d) |
| 26 | 2-tert.-butyl-1,3-dioxepan-5-yl | H | n-propyl | ethyl | 0.9 (s), 1.3 (t), 2.9 (m) |
| 27 | 2-tert.-butyl-1,3-dioxepan-5-yl | H | n-propyl | allyl | |
| 28 | 2-tert.-butyl-1,3-dioxepan-5-yl | H | ethyl | allyl | |
| 29 | 2-tert.-butyl-1,3-dioxepan-5-yl | H | ethyl | ethyl | 0.9 (s), 1.15 (t), 1.7 (m) |
| 30 | 2-(1-ethyl-n-pentyl)-di-1,3-oxepan-5-yl | H | ethyl | ethyl | |
| 31 | 2-(ethyl-n-pentyl)-di-1,3-oxepan-5-yl | H | ethyl | allyl | |
| 32 | 2-(1-ethyl-n-pentyl)-di-1,3-oxepan-5-yl) | H | n-propyl | allyl | |
| 33 | 2-(1-ethyl-n-pentyl)-di-1,3-oxepan-5-yl) | H | n-propyl | ethyl | |
| 34 | 2-(1,2-dimethyl-n-butyl)-1,3-dioxepan-5-yl | H | ethyl | ethyl | |
| 36 | 2-(1,2-dimethyl-n-butyl)-1,3-dioxepan-5-yl | H | n-propyl | ethyl | |
| 37 | 2-(1,2-dimethyl-n-butyl)-1,3-dioxepan-5-yl | H | n-propyl | ethyl | |
| 38 | 2-cyclohexyl-1,3-di-oxepan-5-yl | H | n-propyl | ethyl | |
| 39 | 2-cyclohexyl-1,3-di-oxepan-5-yl | H | n-propyl | allyl | |
| 40 | 2-cyclohexyl-1,3-di-oxepan-5-yl | H | ethyl | allyl | |
| 41 | 2-cyclohexyl-1,3-di-oxepan-5-yl | H | ethyl | ethyl | |
| 42 | 2-cyclododecyl-1,3-di-oxepan-5-yl | H | ethyl | ethyl | |
| 43 | 2-cyclododecyl-1,3-di- | H | ethyl | allyl | |

-continued

| Compound no. | A | R¹ | R² | R³ | ¹H-nmr data (δ values)/$n_D$/m.p. |
|---|---|---|---|---|---|
| | oxepan-5-yl | | | | |
| 44 | 2-cyclododecyl-1,3-dioxepan-5-yl) | H | n-propyl | allyl | |
| 45 | 2-cyclododecyl-1,3-dioxepan-5-yl) | H | n-propyl | ethyl | |
| 46 | 2-(2,6,6-trimethylbicyclo-[3.1.1]-heptan-3-yl)-1,3-dioxepan-5-yl | H | n-propyl | ethyl | |
| 47 | 2-(2,6,6-trimethylbicyclo-[3.1.1]-heptan-3-yl)-1,3-dioxepan-5-yl | H | n-propyl | allyl | |
| 48 | 2,2-pentamethylene-1,3-dioxepan-5-yl | H | n-propyl | ethyl | 1.35 (t), 2.3 (m), 3.7 (m) |
| 49 | 2,2-pentamethylene-1,3-dioxepan-5-yl | H | n-propyl | allyl | 1.6 (m), 4.55 (d), 6.0 (m) |
| 50 | 2-i-propyl-1,3-dioxepan-5-yl | COOCH₃ | ethyl | allyl | |
| 51 | 2-i-propyl-1,3-dioxepan-5-yl | COOCH₃ | ethyl | ethyl | |
| 52 | 2-methyl-1,3-dithiolan-2-yl | H | n-propyl | ethyl | $n_D^{21}$ = 1.5705 |
| 53 | 2-methyl-1,3-dithiolan-2-yl | H | n-propyl | allyl | $n_D^{21}$ = 1.5754 |
| 54 | 2-methyl-1,3-dithiolan-2-yl | H | n-propyl | 3-chloroallyl | $n_D^{23}$ = 1.5829 |
| 55 | 2-methyl-1,3-dithian-2-yl | H | n-propyl | ethyl | 0.98 (t), 1.32 (t), 1.60 (s), 4.11 (g) |
| 56 | 2-methyl-1,3-dithian-2-yl | H | n-propyl | allyl | 0.96 (t), 1.60 (s), 4.0 (m), 5.30 (m), 5.9 (m) |
| 57 | 2-methyl-1,3-dithian-2-yl | H | ethyl | allyl | 1.18 (t), 1.61 (s), 4.53 (d), 5.3 (m), 5.9 (m) |
| 58 | 2-methyl-1,3-dithian-2-yl | H | ethyl | 3-chloroallyl | 1.13 (t), 1.60 (s), 6.63 (m), 6.2 (m) |
| 59 | 2-methyl-1,3-dithian-2-yl | H | n-Propyl | 3-chloroallyl | 0,96 (t), 1,58 (s), 4,60 (m) 6.20 (m) |
| 60 | 2-methyl-1,3-dithian-2-yl | H | ethyl | ethyl | 1.18 (t), 1.35 (t), 1.62 (s), 4.11 (g) |
| 61 | 2-isopropyl-1,3-dioxepan-5-yl | H | ethyl | allyl | 1.1 (t), 2.9 (q), 4,55 (d) |
| 62 | 2-isopropyl-1,3-dioxepan-5-yl | H | ethyl | propargyl | 1.1 (t), 2.5 (s), 4.7 (d) |
| 63 | 2-isopropyl-1,3-dioxepan-5-yl | H | ethyl | 3-chloroallyl (trans) | 1.1 (t), 4.2 (m), 4.5 (d) |
| 64 | 2-isopropyl-1,3-dioxepan-5-yl | H | ethyl | 3-chloroallyl (cis) | 1.1 (t), 1.65 (d), 4.75 (d) |
| 65 | 2,2-pentamethylene-1,3-dioxepan-5-yl | H | n-propyl | propargyl | 1.0 (t), 3.7 (m), 4.6 (m) |
| 66 | tetrahydropyran-4-yl | H | n-propyl | 3-chloroallyl (trans) | 0.95 (t), 2.8 (t), 4.5 (d) |
| 67 | tetrahydropyran-4-yl | H | ethyl | 3-chloroallyl (trans) | 1.1 (t), 3.4 (t), 4.5 (d) |
| 68 | 3-methyl-tetrahydropyran-4-yl | H | ethyl | ethyl | |
| 69 | 3-methyl-tetrahydropyran-4-yl | H | ethyl | allyl | |
| 70 | 3-methyl-tetrahydropyran-4-yl | H | ethyl | 3-chloroallyl (trans) | |
| 71 | 3-methyl-tetrahydropyran-4-yl | H | n-propyl | ethyl | |
| 72 | 3-methyl-tetrahydropyran-4-yl | H | n-propyl | allyl | |
| 73 | 3-methyl-tetrahydropyran-4-yl | H | n-propyl | 3-chloroallyl (trans) | |
| 74 | 5,5-dimethyl-1,3-dioxan-2-yl | H | n-propyl | propargyl | 0.7 (s), 1.15 (s) |
| 75 | 5,5-dimethyl-1,3-dioxan-2-yl | H | n-propyl | 3-chloroallyl (cis) | 0.7 (s), 0.95 (t), 4.75 (d) |
| 76 | 5,5-dimethyl-1,3-dioxan-2-yl | H | n-propyl | 3-chloroallyl (trans) | 0.7 (s), 0.95 (t), 4.50 (d) |
| 77 | 5,5-dimethyl-1,3-dioxan-2-yl | H | ethyl | ethyl· | 1.3 (t), 4.10 (q), 4.35 (s) |
| 78 | 5,5-dimethyl-1,3-dioxan- | H | ethyl | allyl | 1.2 (s), 4.35 (d), 4.5 (d) |

| Compound no. | A | R¹ | R² | R³ | ¹H-nmr data (δ values)/$n_D$/m.p. |
|---|---|---|---|---|---|
| 79 | 2-yl 5,5-dimethyl-1,3-dioxan-2-yl | H | ethyl | 3-chloro-allyl (cis) | 2.9 (m), 3.6 (d), 4.8 (d) |
| 80 | 5,5-dimethyl-1,3-dioxan-2-yl | H | ethyl | 3-chloro-allyl (trans) | 1.1 (t), 34 (d), 4.55 (d) |
| 81 | 5,5-dimethyl-1,3-dioxan-2-yl | H | ethyl | propargyl | 1.2 (s), 2.5 (s), 4.65 (d) |

The cyclohexane-1,3-dione derivatives of the formula I, and their salts, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 2 is mixed with 10 parts by weight of N-methyl-alpha-pyrrolidone. A mixture is obtained which is suitable for application in the form of very fine drops.

II. 20 parts by weight of compound no. 3 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 17 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 12 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 52 is intimately mixed with 97 parts by weight of particulate kaolin. A dust is obtained containing 3% by weight of the active ingredient.

VII. 30 parts by weight of compound no. 67 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 6 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well when they are applied postemergence, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated and their growth stage, and varies from 0.025 to 3 kg/ha and more, but is preferably from 0.05 to 0.5 kg/ha.

The herbicidal action of the cyclohexane-1,3-dione derivatives of the formula I is demonstrated in greenhouse experiments.

The vessels employed were plastic flowerpots having a volume of 300 cm³, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or supended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. The application rates for postemergence treatment varied from 0.03 to 0.25 kg of active ingredient per hectare.

The pots were set up in the greenhouse—species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Alopecurus myosuroides, Avena fatua, Beta vulgaris, Bromus inermis, Bromus spp., Digitaria sanguinalis, Echinochloa crusgalli.* Glycine max., *Hordeum vulgare, Lolium multiflorum, Oryza sativa. Setaria italica, Sinapis alba, Triticum aestivum, Zea mays,* and *Sorghum halepense.*

The following cyclohexane-1,3-dione derivatives disclosed in European Laid-Open Application EP-OS No. 00 71 707 were used as comparative agents:

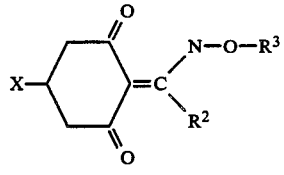

| No. | X | R² | R³ |
|---|---|---|---|
| I | 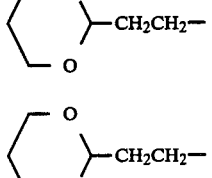 | n-C₃H₇ | C₂H₅ |
| II | 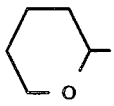 | n-C₃H₇ | —CH₂CH=CH₂ |
| III | 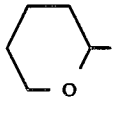 | n-C₃H₇ | C₂H₅ |
| IV | 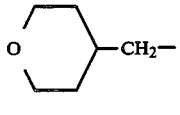 | n-C₃H₇ | C₂H₅ |
| V | 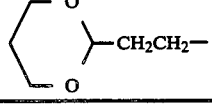 | n-C₃H₇ | —CH₂CH=CH₂ |
| VI |  | n-C₃H₇ | —CH₂CH=CHCl |

The application rates employed for these comparative agents were the same as those for the compounds according to the invention.

Preemergence application:

On preemergence application, for example compounds nos. 7, 53, 2, 1, 17, 54, 10, 12, 20, 23, 29, 57, 59 and 60, applied at a rate of 3.0 kg/ha, proved to be herbicidally effective on plants from the Gramineae family. The broad-leaved test plant Sinapis alba remained undamaged.

Postemergence application:

On postemergence application of 0.25 kg/ha, for instance of compounds nos. 1, 11, 12, 13 and 17, certain grassy unwanted plants or crop plants from the Gramineae family growing in certain locations where they are undesired are combatted better than by comparative agents I and III. Soybeans, as an example of a broad-leaved crop, were not damaged. Compound no. 14, at 0.25 kg/ha, had a superior action to comparative agent VI on Sorghum halepense, and was fully tolerated by soybean plants.

Componds nos. 2 and 3, for example at a rate of 0.125 kg/ha, had a very good—superior to comparative agents IV and V—herbicidal action on Gramineae such as wheat (as volunteer wheat) and Bromus spp. The agents are selective in sugarbeets. Compounds nos. 52 and 53 also combatted grass species very well at 0.125 kg/ha. At this application rate, for instance compounds nos. 26, 29 and 55 had a good action on grasses and caused no damage to wheat, which was significantly injured by comparative agent I. Compound no. 7 combatted barnyardgrass as an unwanted grass species in rice, which remained undamaged (in contrast to treatment with comparative agent I).

Compound no. 6, in addition to being selective in broadleaved crops, had, at a low application rate, a considerable action on grasses and caused no damage to wheat. Comparative agent II inflicted heavy damage on this crop. Compound no. 67, also at a low application rate, excellently combatted unwanted grasses of widely varying vegetation zones—including volunteer species from the Gramineae family. The herbicidal action of compound no. 67 is significantly superior to that of comparative agent IV.

In view of their tolerance by crop plants and the numerous application methods possible, the compounds according to the invention may be used in a further large number of crops for removing unwanted wild grasses or grassy crop plants growing where they are not desired.

The following crops may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | Jerusalem artichoke |
| Hevea brasiliensis | rubber plants |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Phaseolus lunatus | limabeans |
| Phaseolus mungo | mungbeans |
| Phaseolus vulgaris | snapbeans, green beans, dry beans |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize (post-directed only) |

To increase the spectrum of action and to achieve synergistic effect, the cyclohexane-1,3-dione derivatives of the formula I may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, other cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexane-1,3-dione derivative of the formula

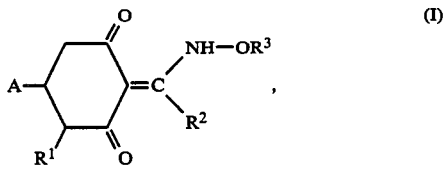

where A is tetrahydropyran-4-yl, 3-methyltetrahydropyran-4-yl, 1,4-dioxanyl, 5,5-dimethyl-1,3-dioxan-2-yl, 2,5-dimethyl-1,4-dioxan-3-yl, 2,6-dimethyl-1,4-dioxan-3-yl, 2-methyl-1,3-dithiolan-2-yl, 2,6-dimethyltetrahydrothiopyran-3-yl or 2-methyl-1,3-dithian-2-yl, or is 1,3-dioxepan-5-yl which is unsubstituted or substituted by alkyl of 1 to 8 carbon atoms, by alkylene of 4 or 5 carbon atoms or by unsubstituted or methyl-substituted cycloalkyl or bicycloalkyl of 6 to 12 carbon atoms, $R^1$ is hydrogen or methoxycarbonyl, $R^2$ is alkyl of 1 to 4 carbon atoms and $R^3$ is alkyl of 1 to 4 carbon atoms, alkenyl of 3 or 4 carbon atoms, haloalkenyl of 3 or 4 carbon atoms and 1 to 3 halogen substituents, or propargyl, and salts thereof.

2. A cyclohexane-1,3-dione derivative of the formula I as claimed in claim 1, where $R^1$ is hydrogen.

3. A cyclohexane-1,3-dione derivative of the formula I as claimed in claim 1, where $R^2$ is alkyl of 2 or 3 carbon atoms.

4. A cyclohexane-1,3-dione derivative of the formula I as claimed in claim 1, where A is tetrahydropyran-4-yl, 2,6-dimethyltetrahydrothiopyran-3-yl or 1,3-dioxepan-5-yl which is unsubstituted or substituted by alkyl of 1 to 8 carbon atoms, alkylene of 4 or 5 carbon atoms, or by unsubstituted or methyl-substituted cycloalkyl or bicycloalkyl of 6 to 12 carbon atoms.

5. A cyclohexane-1,3-dione derivative of the formula I as claimed in claim 1, where A is tetrahydropyran-4-yl, $R^1$ is hydrogen, $R^2$ is ethyl and $R^3$ is 3-chloroallyl (trans).

6. A herbicide containing inert additives and a herbicidally effective amount of cyclohexane-1,3-dione derivative of the formula I as claimed in claim 1.

7. A herbicide as claimed in claim 6, wherein the content of cyclohexane-1,3-dione derivative is from 0.1 to 95 wt %.

8. A herbicide as claimed in claim 6, containing a cyclohexane-1,3-dione derivative of the formula I where A is tetrahydropyran-4-yl, 2,6-dimethyltetrahydrothiopyran-3-yl or 1,3-dioxepan-5-yl which is unsubstituted or substituted by alkyl of 1 to 8 carbon atoms, alkylene of 4 or 5 carbon atoms, or by unsubstituted or methyl-substituted cycloalkyl or bicycloalkyl of 6 to 12 carbon atoms.

9. A herbicide as claimed in claim 6, where the cyclohexane-1,3-dione derivative of the formula I is one in which $R^1$ is hydrogen.

10. A process for combatting the growth of unwanted plants, wherein the unwanted plants or the area to be kept free from unwanted plant growth are treated with a herbicidally effective amount of a cyclohexane-1,3-dione derivative of the formula I as claimed in claim 1.

* * * * *

UNITED STATES PATENT AND TRADEMARK OFFICE
CERTIFICATE OF CORRECTION

PATENT NO.: 4,654,073

DATED: March 31, 1987

INVENTOR(S): JAHN et al.

It is certified that error appears in the above-identified patent and that said Letters Patent is hereby corrected as shown below:

On the cover page, the notice should read as follows:

--[*] Notice: The portion of the term of this patent subsequent to May 20, 2002, has been disclaimed.--

Signed and Sealed this

Twenty-seventh Day of April, 1999

Q. TODD DICKINSON

Attest:

Attesting Officer

Acting Commissioner of Patents and Trademarks